United States Patent [19]
Raboy

[11] Patent Number: 6,111,168
[45] Date of Patent: *Aug. 29, 2000

[54] LOW PHYTIC ACID MUTANTS AND SELECTION THEREOF

[75] Inventor: Victor Raboy, Bozeman, Mont.

[73] Assignee: The United States of America as represented by the Secretary of Agriculture, Washington, D.C.

[*] Notice: This patent is subject to a terminal disclaimer.

[21] Appl. No.: 08/810,898

[22] Filed: Mar. 5, 1997

Related U.S. Application Data

[63] Continuation of application No. 08/215,065, Mar. 17, 1994, Pat. No. 5,689,054.

[51] Int. Cl.[7] ............................... A01H 3/00; A01H 4/00; A01H 5/00; C12N 15/00
[52] U.S. Cl. ...................... 800/312; 800/295; 800/276; 800/298
[58] Field of Search ................................. 800/200, 155, 800/230, DIG. 55, DIG. 17, DIG. 26, DIG. 23, 295, 276, 298, 312

[56] References Cited

PUBLICATIONS

JSimmonds, N.W. Principles of Crop improvement. (1979). Longman, London. pp. xiv–408, 1979.

Thies, W. Determination of phytic acid and sinapic acid esters in rapeseed and selection of geneotypes with reduced concentrations of these compounds. Fett. Wiss. Technol. (1991), 93(2), 49–52.

*Primary Examiner*—Lynette R. F. Smith
*Assistant Examiner*—Thomas Haas
*Attorney, Agent, or Firm*—M. Howard Silverstein; Curtis P. Ribando; John D. Fado

[57] ABSTRACT

Single-gene, non-lethal mutations responsible for low phytic acid-containing seeds are selectable by means of a method for assaying seeds which are otherwise phenotypically, or nearly phenotypically, normal. Maize mutants having from 20% to 95% reductions in kernel phytic acid phosphorus compared to the wild-type, without any noticeable reduction in total phosphorus, were isolated by this method. Mutants obtained in accordance with the invention are useful for developing commercial, low phytic acid seed, plant lines.

5 Claims, 3 Drawing Sheets

WT      lpa1      lpa2

*Fig. 2B* lpa1      lpa2      91286-15

LOW PHYTIC ACID MUTANTS AND SELECTION THEREOF

This application is a continuation of application number 08/215,065, filed Mar. 17, 1994, now U.S. Pat. No. 5,689,054.

BACKGROUND OF THE INVENTION

1. Field of the Invention

Improving human and farm-animal nutrition, and reducing the environmental impact of agricultural production (as part of efforts to improve sustainability), are two highly ranked research goals. Cereal and legume-derived dietary phytic acid (myo-inositol 1,2,3,4,5,6-hexakisphosphate) impacts both areas.

Phytic acid is the major form of phosphorus (P) in seeds, typically representing from 65% to 80% of seed total P [Raboy, "Biochemistry and Genetics of Phytic Acid Synthesis". in Moore D. J., W. Boss, F. A. Loewus (eds). *Inositol Metabolism in Plants*, Alan R. Liss, New York. pp52–73 (1990)]. When seed-based diets are consumed by non-ruminants, the consumed phytic acid forms salts of several nutritionally important minerals in the intestinal tract. Excretion of these salts reduces the retention and utilization (ie. the bioavailability) of both their P and mineral contents. This phenomenon has been documented to contribute significantly to mineral deficiencies in both human and farm-animal populations [McCance et al., *Biochem. J.* 29:4269 (1935); Erdman, *Cereal Chem.* 58:21 (1981)]. Recently there has been growing concern over the contribution of animal-waste phytic acid P to surface and ground-water pollution [Jongbloed et al., *Nether. J. Ag. Sci.* 38:567 (1990)]. Kernel phytic acid P is also a problem in industrial uses such as wet milling, where it precipitates in the concentrated steep water, causing problems in handling, transportation and storage [Pen et al., *Bio/tech.* 11:811 (1993)].

Dietary phytic acid may also play positive roles, such as the inhibition of colonic cancer [Graf, *Nutr. and Cancer* 19:11 (1993)]. Thus, the relative merits or demerits of dietary phytic acid probably depends upon the population in question (ruminant vs. non-ruminant, human vs. farm animal) and the level of phytic acid in the staple diet. For example, in cases where the diet is high in phytic acid and the animal life span is short (such as in poultry and swine production), large reductions in dietary phytic acid may be desirable to improve mineral retention and reduce phosphate waste. In cases where life-span is long, but high dietary phytic acid is causing severe mineral deficiency, such as in numerous human populations in non-industrial societies, perhaps moderate reductions in dietary phytic acid would be desirable. In cases where life-span is long and dietary phytic acid is low, such as in certain industrial societies, increases in dietary phytic acid may be preferred.

This invention represents a novel approach to solving the aforementioned problems caused by phytic acid. A method is disclosed for isolating heritable low phytic acid (lpa) mutants of agronomically important seed crops. The mutants are the products of mutations which cause substantial reductions in kernel phytic acid but which have little effect on other plant or kernel characteristics, including kernel total P.

2. Description of the Prior Art

Several approaches to reducing the impact of dietary phytic acid on P and mineral retention, or reducing the problems caused by kernel phytic acid in industrial applications, such as wet-milling have been proposed or used. These approaches can be viewed as falling into two categories: 1) those which remove dietary phytic acid post-harvest; 2) those which attempt to reduce seed phytic acid content genetically, so that the initial product is improved and therefore does not require post-harvest technologies. The first category includes: food processing methods that remove phytic acid, either physically or via fermentation [Indumadhavi et al., *Int. J. Food Sci. Tech.* 27:221. (1992)]; and, more prominently, the use of phytases (phytic acid-specific phosphohydrolases typically of microbial origin) as dietary supplements [Nelson et al., *J. Nutr.* 101:1289 (1971)]. Pen et al. (WO91/14782) described transforming plants with constructs comprising a gene encoding phytase. Transgenic seed or plant tissues expressing phytases are then used as dietary supplements. Genetically reducing seed phytic acid was not mentioned as an objective of this technology and the effect of transformation with fungal phytases on seed phytic acid was not measured.

The second category involves developing crop germplasm possessing heritable reductions in seed phytic acid. Heritable, quantitative variation in seed phytic acid has been observed among lines of several crop species (reviewed in Raboy, supra). However, this variation has been found to be highly and positively correlated with variation in both plant and seed P, seed protein, and to a lesser extent seed mineral cation concentrations. Up to now, little or no heritable variation in these close and positive relationships has been reported. Therefore, breeding for reduced seed phytic acid using conventional breeding methods (some form of recurrent selection), would very likely result in germplasm having undesirable correlated characteristics. In any case, there have been no reports of "low phytic acid" or "phytic acid-free" germplasm, produced by such an approach, in use.

Recently it was proposed that a seed-specific block in phytic acid accumulation might be valuable in producing low phytic acid germplasm without introduction of undesirable correlated responses [Raboy et al., *Crop Sci.* 33:1300 (1993)]. At maturity the "wild-type" maize kernel typically contains about 3.5 mg/g phytic acid P, representing about 75% to 80% of kernel total P, and about 0.1 to 0.5 mg/g (0.2–1% total P) inorganic P. These values, and those of all phosphorus-containing fractions (total P, phytic acid P, inorganic P) throughout this disclosure are expressed as their phosphorus (P) content (MW 31), as opposed to their phosphate ($PO_4H_3$) content (MW 98). The remaining kernel P is referred to as "cellular P". Phytic acid P usually represents greater than 95% of a mature maize kernel's water-extractable P. Phytic acid deposition is highly localized in the maize kernel. It accumulates in the aleurone layer (<20%), and the germ (>80%): ie. tissues peripheral to the endosperm. A survey of maize "defective kernel" (DEK) mutants, using the same "high-voltage paper electrophoresis" (HVPE) method described in the Examples below, revealed that those mutations which perturb germ and/or aleurone development often are associated with reductions in kernel phytic acid P, and that in all but one case these reductions are accompanied by equivalent increases in kernel inorganic P [Raboy et al., Maydica 35:383 (1990)]. The only exceptions are the viviparous (vp) mutants, in which precocious germination can also result in transient accumulations of the lower inositol phosphates (myo-inositol mono-, bis, tris, tetrakis, and pentakisphosphates). In all those cases, homozygosity for DEK mutants associated with substantial reductions in phytic acid proved to be lethal. Therefore, such mutants are not of any obvious agronomic value.

SUMMARY OF THE INVENTION

I have now discovered that it is possible to isolate single-gene, non-lethal lpa mutants which cause substantial reductions in seed phytic acid P, but have no other obvious or substantial effects. As evidence of this discovery, lpa maize mutants having up to 95% reduction in kernel phytic acid P compared to the wild-type, without any noticeable reduction in total P, were isolated. These mutants can be used to breed "low phytic acid" maize using conventional back-crossing methods. I have also demonstrated the reliability of a simple, rapid and inexpensive method for assaying and selecting other such mutants.

In accordance with these discoveries, it is an object of this invention to provide a general screening procedure for identifying non-lethal lpa mutants in seed of any plant species, especially that of agronomically important crops.

It is another object of this invention to select for a heritable lpa mutation which does not have a negative effect on other desirable crop characteristics.

Another object of this invention is to isolate lpa mutants which would be useful in breeding programs for generating commercial lines of low phytic acid crops.

A further object of the invention is to provide for the first time maize mutants which represent a locus perturbation (single-gene mutation) resulting in the lpa phenotype.

These and other objects of the invention will become readily apparent from the ensuing description.

BRIEF DESCRIPTION OF THE DRAWINGS

FIG. 2 illustrates a colorimetric assay based on the "High Inorganic P" (HIP) phenotype of lpa mutants.

DEPOSIT OF BIOLOGICAL MATERIAL

Seeds of lpa1 (lpa1-1) and lpa2 (lpa2-1) *Zea mayes* mutant homozygotes described herein were deposited on Aug. 15, 1996, under the terms of the Budapest Treaty at the American Type Culture Collection, 12301 Parklawn Drive, Rockville, Md. 20852, USA, and have been assigned Accession Nos. ATCC 97678 and ATCC 97679, respectively.

DETAILED DESCRIPTION OF THE INVENTION

The methods of this invention have been illustrated herein for selecting and identifying non-lethal, low phytic acid mutants of *Zea mays*, commonly referred to as maize or corn. However, based on the results obtained for maize, these methods are contemplated to be fully applicable to all agronomically important seed crops such as the cereals, legumes, and oil seed crops. Cereal crops of particular interest besides maize include wheat, barley, sorghum, rice, and oats.

Of course, the principal legume of interest is soybean.

The methods of the invention are designed to screen for low phytic acid phenotypes which are otherwise phenotypically normal, or near normal. The occurrence of low phytic acid accumulation in mature seeds is a recessive trait, and therefore phenotypic lpa seeds identified by the screen will be homozygous for the recessive allele. Though evidence is presented herein that the mutation for the recessive allele occurs in nature as an infrequent event, the screening method of the invention is most expeditiously conducted on seeds derived from mutagenesis of at least one of the seeds' precursive sporophytes or gametophytes. The method illustrated herein utilizes maize pollen mutagenesis. Given that the pollen grain is haploid, any induced mutation at a given locus would give rise to a heterozygous genotype in the resulting seed (M1 generation). It thereby becomes necessary to grow out the plant from each putatively mutated seed, self-pollinate the resulting plants and assay a sampling of the seed (M2 generation) from each plant for the mutant phenotype. The mutation will segregate according to the Mendelian distribution (1:2:1) and the ratio of wild-type phenotype mutant phenotype will be in the ratio of 3:1. Insofar as most end-uses for seed where phytic acid is a concern involve the mature seed, it is envisioned that the assays described herein will be conducted on fully mature seed. Mature seed is defined as that which has reached physiological maturity and is capable of germination, whether or not it has been dried. This is also the common state of seed harvested for food or feed. It is believed that, for most seeds, phytic acid accumulates during the course of development; and, in some cases, there would be an interest in the phytic acid content of seeds at various stages of maturity. For example, sweet corn and green peas are harvested at an immature stage for consumption. Therefore, the assays of the invention could also be conducted on immature seed, that is, seed which has not reached full physiological development.

For purposes of the ensuing discussion, the parent plant producing either the mutagenized gamete or the gamete mated to the mutagenized gamete will be referred to as "M0". The progeny of plants grown from M0 and self-pollinated will be referred to as "M1". The genotype of these progeny will either be homozygous wild-type or heterozygous, and all such progeny will be phenotypically wild-type. The progeny of plants grown from M1 and self-pollinated will be referred to as "M2", approximately one fourth of which will manifest the lpa phenotype.

Mutagenesis is effected by any conventional means in the art which will not be lethal to all the treated germ cells. The most common methods include irradiation, chemical treatment, and transposable element insertion. The procedure used herein for mutating maize is described by Neuffer et al. [*Maize for Biological Research* ed. by W. F. Sheridan, Plant Molecular Biology Association (1982)]. In accordance with this method, wild-type pollen is treated with ethyl methanesulfonate (EMS), and the treated pollen is applied to silks of wild-type plants. The resulting "M1" kernels are therefore heterozygous for one or more random mutations. These kernels are planted, and the resulting plants are self-pollinated, producing M2 progenies (ears) each of which is segregating for one or more mutations.

The novelty of the invention resides in the discovery that it is possible for the lpa phenotype to not only be non-lethal, but also for the seed to be nearly phenotypically identical to wild-type seed. These discoveries were unpredictable and arose from a systematic assay of M2 maize kernels which appeared normal and were not expected prior to assay to be homozygous for lpa. In screening seed for the lpa phenotype, any indicator of phytic acid content can be used. As described in further detail below, both phytic acid P and inorganic P are convenient indicators for this purpose.

The initial screen for mutant homozygotes in the study leading to this invention was conducted using the HVPE method of [Raboy et al. *Maydica* 35:383 (1990)] described above. That method relies upon differential migration of the cellular phosphorus compounds including the various forms of phosphorylated myo-inositol and inorganic P. The chromatogram of the electrophoretically-fractionated phosphorus-containing compounds permits a semi-quantitative assessment of phytic acid relative to the other compounds. Once specific non-lethal lpa maize mutants were identified, it was then possible to establish that the total seed P content typical of the wild-type is conserved in the mutants and that what is lost as phytic acid P in the wild-type is gained in the mutant as inorganic P. Thus, another aspect of this invention is the discovery that M2 seeds can be screened for lpa mutants by assaying for high levels of inorganic P. In many plant species, the phytic acid is distributed in some fashion throughout both the germ and endosperm tissues. Any mutation which effects a significant reduction in the endosperm phytic acid can be identified by nondestructive assay of the endosperm tissue. If a destructive assay of the germ is undertaken, then the mutant phenotype can be propagated from remnant seed of siblings.

The assay employed in the selection method of this invention can be designed to select for any predetermined level of phytic acid reduction or inorganic P increase. For purposes of this invention, any phenotype which has reduced phytic acid as compared to the wild-type from which it was derived at a statistically significant level is considered to be a lpa mutant. In general, the reduction in phytic acid should be at least 20% in order to be considered as having agronomic importance. In the case of the lpa1 mutant described in further detail in the Examples, below, phytic acid P was reduced to about 32% of its original level in the wild-type. The inorganic P for this mutant was increased approximately nine-fold. The change in P distribution for the lpa2 mutant was less dramatic. Its phytic acid P level was about 76% of that of the wild-type, and the inorganic P level increased nearly four-fold.

It will appreciated by those skilled in the art of plant genetics that lpa mutants isolated by the methods of this invention, though phenotypically very similar to the wild-type, would usually need to be introduced into a breeding program in order to introduce the low phytic acid trait into a commercial line. This is typically accomplished by first selfing plants from the M2 seeds through four or five generations to obtain germplasm which is nearly uniformly homozygous for the lpa trait. These plants (donor inbred) are then crossed with a commercial line (a superior inbred), and the progeny of that cross repeatedly backcrossed to the superior inbred until the commercial line breeds true for lpa.

As discussed in Example 4, below, the lpa1 and the lpa2 maize mutants disclosed herein are characterized by a small kernel dry weight reduction. Assuming there is indeed a causal relationship between lpa genotype and kernel dry weight reduction, this could translate into a reduction in productivity if unresolved. In addition, it is possible that homozygosity for a given lpa mutant might impact other characteristics of agronomic importance, such as seed storage, germination (under less than optimal conditions), and susceptibility to pathogens. Single-gene mutants useful for sweet corn and high-lysine corn also have associated agronomic deficits such as impaired germination and reduced productivity. Developmental efforts similar to those undertaken for those traits could also be applied to low phytic acid phenotypes.

While lpa technology as related to the maize mutants of this invention will probably be useful as it stands, there is no doubt that correction for the dry weight reduction would benefit its commercial acceptability. Two specific approaches to this problem are described below.

The first approach relates to the observation of variation for dry weight reduction among segregating F2 and test-cross individuals (Table 3). Analyses of BC1 (Backcross 1) F2 progenies also revealed substantial variation in the reduction in kernel dry weight associated with lpa1. Assays of eighty kernels sampled from BC1 F2s revealed that the dry weight reduction associated with homozygosity for lpa1 ranged from 13% in one individual (93421-2) to 2% in another individual (93422-16). Perhaps during back-crossing, selection for lpa progenies with nominal kernel dry weights will be routinely possible. If the kernel dry weight reduction is in fact due to factors closely linked to either lpa1 or lpa2, then selection against the dry weight reduction should be feasible.

The second approach is based on the hypothesis that the major contributing factor to the reduction in kernel dry weight is a partial suppression of endosperm carbohydrate synthesis caused by the high inorganic P phenotype of lpa mutants. Endosperm carbohydrate is the major component of kernel dry weight, and a key regulatory step in carbohydrate synthesis in plant cells is catalyzed by ADP-glucose pyrophosphorylase (ATP:α-glucose-1-P adenyl transferase, EC 2.7.7.27). Maize kernel ADP-glucose pyrophosphorylase is allosterically inhibited by increasing inorganic P concentration [Plaxton et al., *Plant Physiol.* 83:105 (1987)]. A mutant *E. coli* ADP-glucose pyrophosphorylase is not allosterically regulated by inorganic P, and it has been demonstrated that this enzyme functions, and increases starch content, in transgenic plant tissues [Stark et al. *Science* 258:287 (1992)]. The alternative approach would be to transform lpa maize with a construct which results in a seed-specific expression of the similar non-regulated ADP-glucose pyrophosphorylases.

EXAMPLE 1

Isolation and Initial Phenotypic Characterization of lpa1 and lpa2

Populations of ethyl methanesulfonate (EMS)-induced mutations in maize were produced in an "Early-ACR" stock using the methods of Neuffer and Coe, supra. Briefly, a 1.0% EMS stock solution was prepared by placing 0.5 ml EMS into 49.5 ml light paraffin oil. Immediately prior to use, this stock solution was stirred for 1.0 hr. Individual treatments were conducted in 50 ml screw-capped polypropylene tubes. Fourteen mls of light paraffin oil was placed in a tube, to which was added 1 ml EMS stock solution and 1 ml pollen. Thus, the treatment solution was 0.063% EMS. Following 45 min of treatment with gentle shaking, treated pollen was applied to silks of untreated plants with a #10 camel hair brush. Each resulting M1 kernel obtained following such a pollination contains one discrete, treated genome (from an individual pollen grain) and one untreated genome (from the egg), and is therefore heterozygous for one or more random mutations. These kernels were planted, and the resulting plants were self-pollinated, producing M2 progenies (sibling kernels on a given ear). Segregation for induced mutations first occurred in these M2 progenies, and was observed in the M2 kernels.

Figure 1:
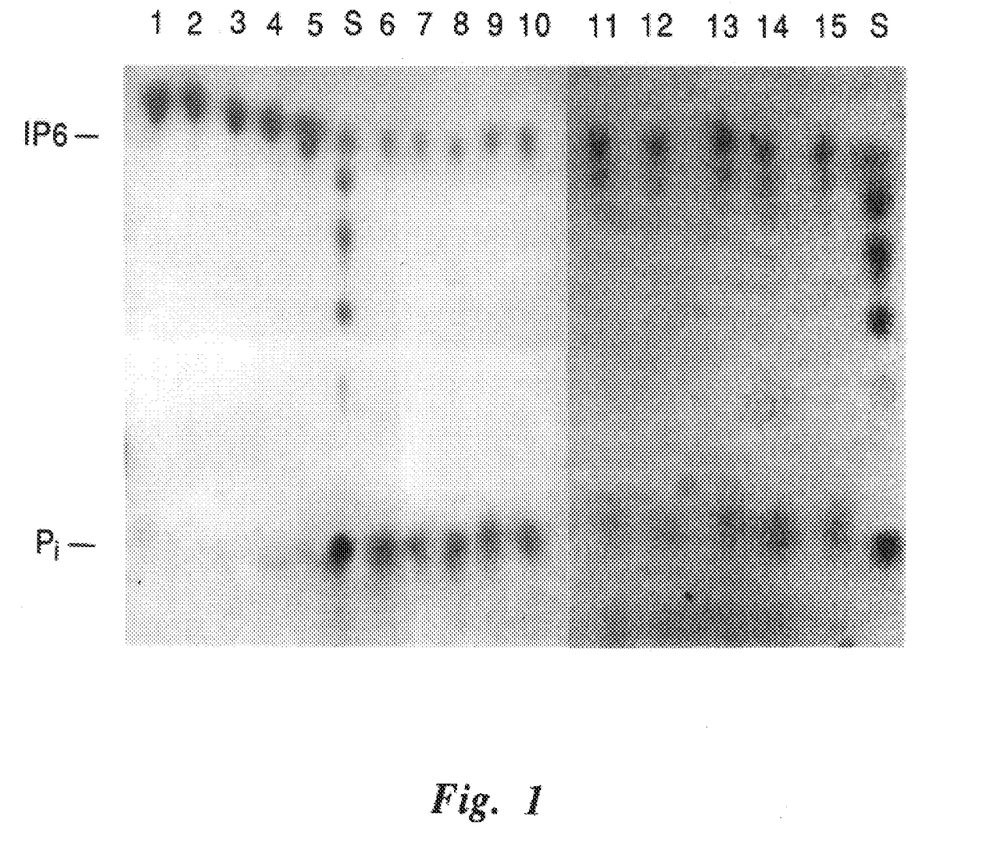
FIG. 1 is a High Voltage Paper Electrophoresis (HVPE) single-kernel analysis showing the HVPE phenotype of maize seed. Lanes 1 through 5 represent tests of wild-type kernels; lanes 6 through 10 represent tests of homozygous lpa1 kernels; and lanes 11 through 15 represent tests of homozygous lpa2 kernels. Lanes marked "S" are standards.

Initially, 938 M2 progenies were screened for lpa mutants with the following HVPE method which provides optimal separation of inositol phosphates and inorganic P. Individual kernels were crushed and extracted in 10 v/w 0.4 M HCl. Ten μl of extract was applied to the origin of a Whatman No. 1 sheet and fractionated electrophoretically (25 V/cm, 2 hrs) in 0.1 M Na oxalate. The chromatogram was dried and stained for phosphate [Haines C. S., Isherwood F. A., *Nature* 164:1107 (1949)] as following. A staining solution was prepared by dissolving 1.25 g ammonium molybdate in 10 ddH$_2$O, adding 5 ml perchloric acid, 1.0 ml conc. HCl, and then dilution to 100 ml with acetone. The chromatogram was dipped in this solution, and then immediately dried at 80° C. Phosphate-containing compounds stain blue, and usually appear overnight. Standards (FIG. 1, lanes "S") contain a mixture of phytic acid (IP6) and in descending order myo-inositol pentakis-, tetrakis-, tris-, and bisphosphate (sometimes not visible to the naked eye), and inorganic P ($P_i$). If one extracts a "wild-type" maize kernel in 10 volumes of 0.4 M HCl, and tests 10 μl with HVPE, one observes an abundant compound representing about 3.5 μg P, which co-migrates with standard phytic acid (FIG. 1, lanes 1 through 5). At this level of sensitivity, trace amounts of inorganic P and no lower inositol phosphates are observed. Kernels which appeared wild-type to the naked eye were sampled from each M2 progeny and tested by HVPE for a phenotype (the HVPE phenotype) displaying either reduced phytic acid, increased lower inositol phosphates, or increased inorganic P.

The first such mutant determined to be an allele at a single gene, lpa1, was initially observed segregating in one M2 progeny, identified as 90046-13. As visualized on the HVPE chromatogram, the lpa1 phenotype is characterized by an approximately two-thirds reduction (as compared with wild-type) in the phytic acid P, accompanied by an apparently equivalent increase in inorganic P (FIG. 1, lanes 6 through 10). The second mutant, lpa2, was first observed in three M2 progenies (90041-1, 90041-4, and 90041-12). These three M2 progenies were obtained from sibling kernels on a single M1 ear (GH90-36). The lpa2 phenotype was not observed in M2 progenies obtained from any of the other 52 M1 ears in this generation. Thus, it appears that this mutation occurred spontaneously in an individual M0 parent, prior to EMS treatment, and was first segregating in an individual M1 progeny. As visualized on the HVPE chromatogram, the lpa2 HVPE phenotype is characterized by an approximately one-third reduction in the phytic acid P (as compared with the wild-type), accompanied by one or two additional spots with mobilities similar to myo-inositol pentakisphosphate, and intermediate between that of myo-inositol tetrakis- and pentakisphosphate (respectively) and an equivalent increase in inorganic P (FIG. 1, lanes 11 through 15).

Forty-five M3 progeny ears were obtained from 90046-13 (lpa1) field-planted kernels. Tests of these M3 progenies indicated that eight M2 plants were homozygous mutant (lpa1/lpa1), nine homozygous wild-type (+/+), and 28 were heterozygous (+/lpa1). These results provided the initial evidence that lpa1 represents an allelic variant at a single locus (Chi-square of 2.73 indicates the data fits the 1:2:1 model for single-gene inheritance with two degrees of freedom) and that homozygosity for the mutant allele had little effect on germination under optimal field conditions.

Kernels from three M3 heterozygotes identified as segregating for lpa1 were planted in a summer field nursery and the resulting plants self-pollinated. Progeny tests of the 172 M4 ears obtained indicated that 34 were homozygous lpa1, 95 were segregating for lpa1, and 43 were homozygous wild-type. This supports the initial results which indicated that lpa1 is an allelic variant at a single gene (Chi-square of 2.82 indicates the data fits the 1:2:1 model for single-gene inheritance with two degrees of freedom), and that homozygosity for lpa1 is not conditionally lethal. Nor were other striking effects on plant phenotype observed to segregate with lpa1.

M2 kernels from 90041-4 (lpa2) were also planted and self-pollinated, and wild-type and mutant homozygotes were identified. Then wild-type, lpa1 and lpa2 homozygotes were planted in the summer nursery, and the resulting plants were self-pollinated, initiating homozygous lines which were used for quantitative analyses given below. In addition, cross pollinations were made between lpa1 and lpa2 homozygotes, and between mutant and wild-type homozygotes, producing F1 heterozygotes. These were used both for quantitative analyses and for subsequent genetic tests described below. All kernels tested from F1 progenies representing crosses between lpa1 and lpa2 homozygotes had wild-type levels of kernel phytic acid, indicating that these are alleles at two distinct loci.

Quantitative analyses of whole kernel samples indicated that both lpa1 and lpa2 homozygotes had total P concentrations similar to wild-type and F1s (Table 1). Total P was determined calorimetrically [Chen et al., *Anal. Chem.* 28:1756 (1956)] following complete digestion of tissue samples with concentrated H$_2$SO$_4$. Phytic acid was determined colorimetrically following complete digestion (conc. H$_2$SO$_4$) of ferric precipitates obtained following extraction in 0.4 M HCl: 10% Na$_2$SO$_4$ (the "ferric-precipitation method"; Raboy et al.; *Maydica*, supra). Inorganic P was determined calorimetrically following extraction (4° C.) in 12.5% TCA: 25 mM MgCl$_2$. Phytic acid P represented from 76% to 79% of kernel total P in wild-type and F1s, 23% of total P in lpa1 homozygotes, and 57% of total P in lpa2 homozygotes. lpa1 and lpa2 conditioned 68% and 24% reductions, respectively, in phytic acid P which corresponds to 51% and 18% of kernel total P. The reductions in kernel phytic acid P associated with lpa1 and lpa2 appeared to be accompanied by molar-equivalent increases in kernel inorganic P. Kernel inorganic P represented 8% of total P in wild-type, 66% of kernel total P in lpa1 homozygotes, and 28% of kernel total P in lpa2 homozygotes. Therefore, the sum of kernel phytic acid P and inorganic P appears to represent a constant, which is approximately 85% of kernel total P.

Initial analyses of both lpa1 and lpa2 heterozygotes (Table 1) revealed no obvious differences in kernel total P, phytic acid P, or inorganic P, as compared with wild-type. This suggests that both lpa1 and lpa2 are recessive alleles at their respective loci. However, subsequent analyses revealed that in the case of lpa1, heterozygote kernel inorganic P is twice that observed in sibling homozygous wild-type kernels. This increase in inorganic P in lpa1 heterozygote as compared with wild-type homozygote is not consistently observed. If when observed it parallels a reduction in phytic acid P, then that reduction would represent about 5%, which is not detectable at the level of sensitivity of the assays used here.

EXAMPLE 2

Effect of lpa Mutants on Kernel Phosphate Distribution

An initial series of experiments was conducted to determine the effect of homozygosity for lpa1 on the distribution of kernel phosphate. Kernels sampled from wild-type and lpa1 homozygotes (two individuals of each) were dissected into two fractions: germ, including embryo and scutellum; and endosperm, including starchy endosperm and aleurone layer. These were weighed and assayed in duplicate for kernel total P, phytic acid P, and inorganic P as described above for whole kernels in Example 1. The entire experiment was repeated twice with similar results and the results of the second experiment are given in Table 2. Homozygosity for lpa1 reduced phytic acid P, and increased inorganic P in both germ and endosperm fractions. Thus, the lpa1 phenotype does not appear to be specific to either fraction. Repeated whole kernel analyses had indicated that two quantities, total P and the sum of phytic acid P and inorganic P (acid-extractable P), appeared to be relatively constant regardless of lpa1 genotype (Table 1). Analyses of kernel fractions revealed that both of these quantities were reduced in lpa1 germs, and increased in lpa1 endosperms, as compared with wild-type. Thus, homozygosity for lpa1 alters both the form and the distribution of P in the kernel. However, the change in distribution is on the order of 10%, while the change in form is on the order of 60%.

EXAMPLE 3

An Assay for lpa Mutants Based on the "High Inorganic P" (HIP) Phenotype

A simple colorimetric assay for inorganic P conducted in microtiter plates was developed to test for lpa genotype. As discussed above, wild-type maize kernels typically contain very low levels of inorganic P. Therefore, if reductions in kernel phytic acid P typically are accompanied by increases in inorganic P, then even small reductions in phytic acid P should be detectable via assays of inorganic P. The large increases in inorganic P conditioned by homozygosity for either lpa1 or lpa2, which are referred to as the "high inorganic P" (HIP) phenotype, are readily distinguishable from either the wild-type or the heterozygote. These large increases in kernel inorganic P permit design of a micro-colormetric HIP assay which permits simple visual inspection for determination of the results (FIG. 2). Alternatively, these assays can be quantified using a spectrophotometer to yield quantitative results. Both visual inspection and spectrophotometric assay have value, depending on the objective and the technology available, for a particular application. For example, on-site tests at field stations conducting back-crossing programs or at grain storage and shipping sites, which are not likely to be equipped with a spectrophotometer, may use an assay designed for visual inspection.

Individual kernels were weighed, crushed, and extracted overnight in 10 v/w 0.4 M HCl at 4° C. with no stirring. Prior to assay, extracts were vortexed. Following settling for 30 min, ten µl of extract was assayed for inorganic P by the method of Chen et al. (supra) modified by reducing the total volume to 200 µl and conducting the assay at room temperature in micro-titre wells. Sample wells contained 10 µl of extract, 90 µl ddH$_2$O, and 100 µl of assay reagent (containing one volume 10% ascorbic acid, one volume 2.5% ammonium molybdate, one volume 6N sulfuric acid, and two volumes ddH$_2$O). Standards were similarly prepared, except that instead of extract they contained either no P, 155 ng P, 465 ng P, 930 ng P, or 1395 ng P (FIG. 2A, 1 through 5 respectively).

Figure 2A:
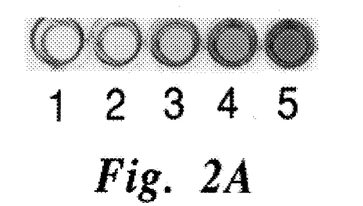
FIG. 2A contains P standards ranging from none (well 1) to 1395 ng P (well 5).
Figure 2B:
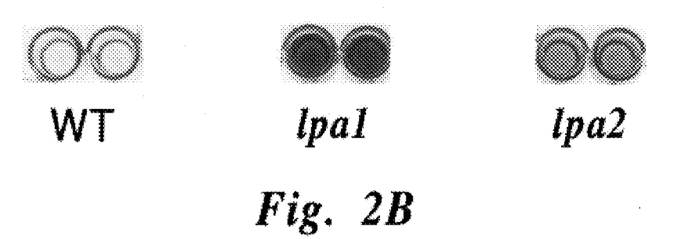
FIG. 2B illustrates tests of two kernels representing wild-type (WT), homozygous lpa1 and homozygous lpa2.
Figure 2C:
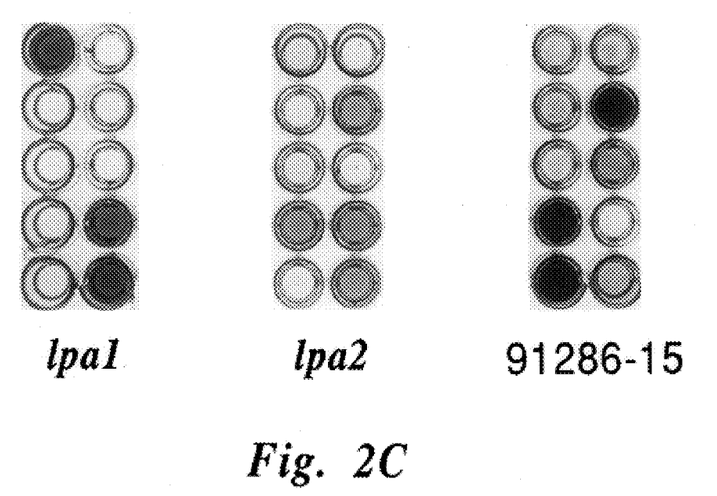
FIG. 2C illustrates tests of ten kernels sampled from ears segregating for lpa1, lpa2, and a novel mutant (91286-15).

FIG. 2B contains two tests each of kernels homozygous wild-type (WT), homozygous lpa1, or homozygous lpa2. Wild-type kernels typically contain from 0.05 to 0.5 mg P as inorganic P per g dry weight. Since in this method a kernel is extracted in 10 volumes per weight (for instance a 200 mg dry weight kernel would be extracted in 2.0 ml), and 10 µl of extract is assayed, then such an assay of a wild-type kernel would typically contain up to 0.5 µg P. Therefore, in the variation of the method described here, a threshold for testing for the HIP phenotype would be the standard containing 465 ng P (FIG. 2A, Well #3). Any assays containing substantially more P would be considered HIP positive. For example, assays of similarly tested lpa1 kernels typically contain from 2.5 µg to 3 µg inorganic P per well, and assays of lpa2 kernels contain from 1.0 µg to 1.5 µg P per well (illustrated in FIG. 2B). The lpa2 levels of inorganic P, assayed as described above, fall within the linear range of a spectrophotometric assay. However, the lpa1 levels often would be beyond the linear range of a spectrophotometric assay. Therefore, a modification of the method as described would be necessary when: 1) the intention is to quantitate these assays with a spectophotometer; or 2) the mutant in question causes an increase in kernel inorganic P as great or greater than that associated with lpa1. The modification would be to extract the kernel in a greater volume or to assay 5 µl rather than 10 µl of extract. FIG. 2C contains tests of ten kernels selected from ears segregating for lpa1, lpa2, and a novel mutant (91286-15, discussed further in Example 5), which causes increases in kernel inorganic P greater than lpa1. The tests given in FIG. 2C illustrate how this method can identify mutant versus wild-type kernel segregants. They also illustrate that in the case of mutants like 91286-15, the HIP assay as described above gives clear results visually, but the level of inorganic P in the micro-titer plate well (about 3.5 µg) is too high for spectrophotometric assay. Therefore, in that instance the spectrophotometric assay would have to be modified as described above.

This HIP assay is a sensitive, accurate, and reproducible assay for lpa mutants, if care is taken to first inspect kernels for the aborted or altered germ phenotype, and for vivipory or premature germination. "Germless" or "aborted germ" mutants are very common, and represent the most: important source of "false-positive" assays in the case of maize. A second source of false-positives is the viviparous mutants. The F2 and test-cross progenies tested (Table 3) contained very few germless or prematurely germinated kernels.

EXAMPLE 4

The Inheritance and Transmission of lpa1 and lpa2 and Their Association with Reductions in Kernel Dry Weight In the initial quantitative analyses (Table 1), kernel dry weight appeared reduced in both lpa1 and lpa2 homozyotes and heterozygotes, as compared with wild-type. Subsequent analyses of reciprocal F1s and additional homozygotes indicated that both lpa1 and lpa2 heterozygotes had kernel dry weights similar to wild-type, but that both lpa1 and lpa2 homozygotes had kernel dry weights reduced about 10% as compared with wild-type. In the analyses of kernel fractions (Table 2), both germ and endosperm dry weights were reduced in lpa1 as compared with wild-type, but the reduction in endosperm dry weight was consistently substantially greater, in terms of its contribution to the total dry weight deduction, than the reduction in germ dry weight.

Analyses of F2 and test-cross progenies were conducted: 1) to study the inheritance of lpa1 and lpa2; and 2) to determine the extent to which the differences in kernel dry weight observed in the analyses of homozygotes was due to maternal effects or due to kernel-specific effects of either lpa1 or lpa2, or of closely linked factors. F1 heterozygotes were planted, and the resulting plants were both self-pollinated, and test-crossed either as a male or female parent by homozygous lpa1 or lpa2 testers.

Table 3 summarizes the results of the F2 and test-cross analyses. In these studies individual kernels were weighed and then tested for lpa genotype. First, every kernel from each of six lpa1 F2 progenies was assayed. The results approximated but did not fit (at the 5% level) the 3:1 (1 degree of freedom) model for the inheritance of an allele at a single gene in an F2 analysis. A trend for a reduced representation of mutant kernels, when compared with the predicted number, was observed. Mutant kernels had a mean dry weight reduction of 10%. Next, 100 kernels from each of six lpa2 progenies were assayed. Of these, four progeny clearly segregated for the characteristic lpa2 phenotype, both in increased inorganic P and a corresponding HVPE phenotype, and the sums and means of the data for these four are given in Table 3. The inheritance of lpa2 fit the 3:1 model for the inheritance of an allele at a single gene. On these ears, mutant kernels had a mean dry weight reduction of 9.3%. Of the remaining two lpa2 F2s, one progeny appeared to segregate for increased inorganic P, but this did not correspond to an altered HVPE phenotype, and in the second progeny all kernels tested appeared wild-type.

In terms of inheritance, initial F2 analyses indicate: 1) that both lpa1 and lpa2 are alleles at single loci; 2) an under-representation of mutant kernels in segregating progenies is observed for lpa1; and 3) while lpa2 clearly appears to be an allele at a single locus, it may be unstable (perhaps due to transposable element insertion), or there may be modifiers which alter its expression, or it may display partial penetrance. However, to date all lpa2 homozygotes have bred true, and clearly display the lpa2 phenotype. These analyses also indicate that the reduction in kernel dry weight associated with lpa1 and lpa2 (Tables 1 and 2) is a kernel-specific trait, either directly caused by the given lpa mutation or due to factors linked with the given lpa mutation.

The analyses of reciprocal test-crosses indicated that transmission of lpa1 through pollen (male gamete) is reduced as compared with transmission through the female gamete. In a test-cross of a heterozygote, one should observe a distribution of wild-type and mutant kernels that approximates 1:1. When the lpa1 allele is transmitted through the pollen (when the F1 heterozygote is used as a male in test-cross), signficantly (5% level of probability) fewer mutant kernels were observed than would be predicted by the 1:1 model. When this mutant was transmitted through the egg, (when the F1 heterozygote was used as a female in a test-cross), the results fit (statistically) the 1:1 model. This would explain the under-representation of mutant off-spring in F2s. No such difference in transmission of lpa2 was observed. These test-cross assays confirmed that both lpa1 and lpa2 are alleles at single loci, and confirmed that the reduction in seed dry weight associated with homozygosity for these mutants is seed-specific and either due to the mutant itself or to tightly linked factors.

EXAMPLE 5

Using the HIP Assay to Isolate Novel lpa Mutants

Figure 3:
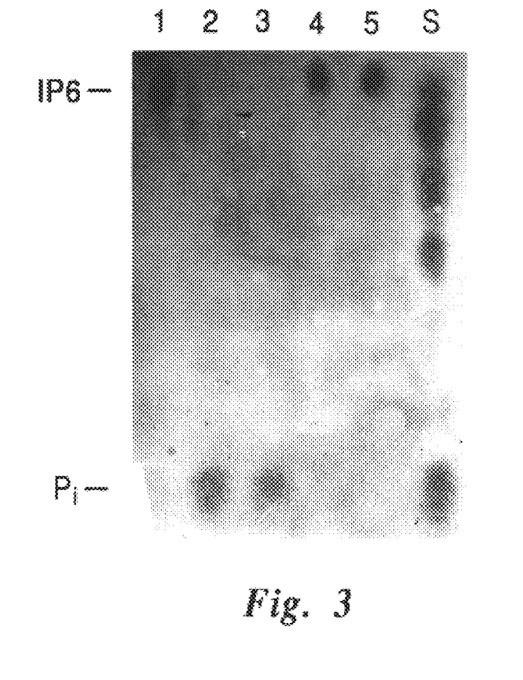
FIG. 3 is an HVPE analysis of five kernels sampled from test ear 91286-15, an M2 progeny segregating for a mutant phenotype (lanes 2 and 3) in which phytic acid appears absent and is estimated to be reduced on the order of 95%.
Figure 4:
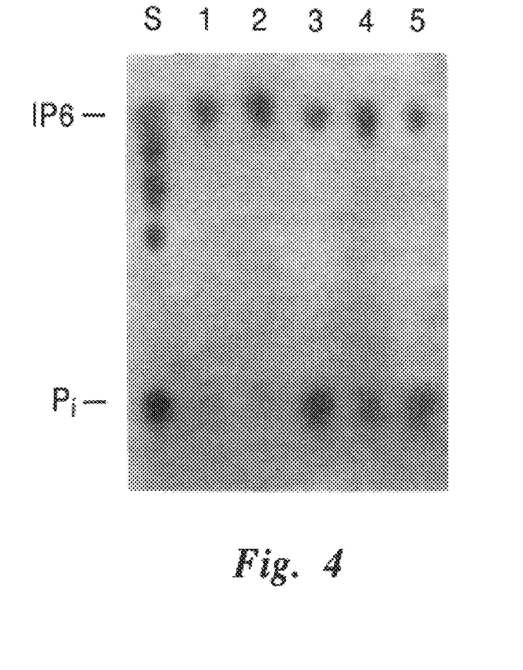
FIG. 4 is an HVPE analysis of five kernels sampled from test ear 92084-6, an M2 progeny segregating for a mutant phenotype (lanes 3 and 5) in which phytic acid is reduced from 20% to 50%.

Over 4500 additional M2 progenies, produced as described above in Example 1, were screened using the HIP assay. Progenies segregating for the HIP phenotype were then tested using HVPE. Using this two-step approach, an additional 49 putative lpa mutants which condition reductions in kernel phytic acid ranging from 95% to about 10% have been isolated. The F3 generation of the first 27 putative mutants are currently being analyzed. Of these, three condition reductions in kernel phytic acid P ranging from 80% to 95% (an example is given in FIG. 3); seven condition reductions similar to that of lpa1 (approximately 66%, like that in FIG. 1, lanes 1 through 5); five condition reductions ranging from 20% to 50% (an example is given in FIG. 4); and one is phenotypically similar to lpa2 (as in FIG. 1, lanes 11 through 15). The remainder may condition reductions of less than 20% and were not of primary interest in this study. Initial tests indicate that in every case, decreases in phytic acid P are accompanied by equivalent increases in inorganic P. In no case were mutants found in which phytic acid was absent. In the case of 91286-15 (FIG. 3), initial HVPE tests indicated the absence of phytic acid; but subsequent tests of concentrated extracts revealed there was a trace of phytic acid. HIP assays indicate that essentially all of the phosphate that is found as phytic acid P in the wild-type, is found in this mutant as inorganic P. With the possible exception of the lpa2-like mutant, in no case were unusual accumulations of lower inositol phosphates observed. The effect on germination, or possible lethality, of these putative mutants is currently being studied. Initial results indicate that nearly all these mutants can be used in simple back-crossing breeding programs to develop maize inbreds and hybrids with almost any level of kernel phytic acid deemed desirable, ranging from essentially none, through intermediate levels as compared with wild type.

TABLE 1

Whole kernel total P, phytic acid P, and inorganic P in
Ipa1 and Ipa2 homozygotes and heterozygotes

| Genotype[a] | Dry Weight mg kernel | Total P mg g$^{-1}$ | Phytic Acid P | | Inorganic P | | Phytic Acid P + Inorganic P | |
|---|---|---|---|---|---|---|---|---|
| | | | mg g$^{-1}$ | % Tot P | mg g$^{-1}$ | % Tot P | mg g$^{-1}$ | % Tot P |
| +/+ | 282 | 4.5 | 3.4 | 76 | 0.34 | 8 | 3.7 | 82 |
| +/Ipa1 | 208 | 4.5 | 3.5 | 78 | 0.46 | 10 | 3.9 | 87 |
| Ipa1/Ipa1 | 238 | 4.7 | 1.1 | 23 | 3.09 | 66 | 4.2 | 89 |
| +/Ipa2 | 265 | 4.3 | 3.4 | 79 | 0.32 | 7 | 3.7 | 86 |
| Ipa2/Ipa2 | 232 | 4.6 | 2.6 | 57 | 1.31 | 28 | 3.9 | 85 |
| SE | 26 | 0.4 | 0.7 | — | 0.28 | — | 0.4 | — |

[a]+/+, wild-type homozygote; +/Ipa1 and +/Ipa2, heterozygotes obtained by polinating +/+ by homozygous mutants; Ipa1/Ipa1 and Ipa2/Ipa2, homozygous mutants.

TABLE 2

Total P, phytic acid P, and inorganic P in germ and endosperm fractions of wild-type and Ipa1 homozygotes

| Genotype[a] | Dry Weight mg | Total P | Phytic Acid P | Inorganic P | Phytic Acid P + Inorganic P |
|---|---|---|---|---|---|
| | | | mg g$^{-1}$ | | |
| Germ | | | | | |
| +/+ | 34 | 27.5 | 26.8 | 0.5 | 27.3 |
| Ipa1/Ipa1 | 30 | 20.7 | 6.2 | 14.3 | 20.5 |
| SE | 2 | 2.4 | 0.9 | 0.7 | 1.1 |
| Endosperm | | | | | |
| +/+/+ | 183 | 0.69 | 0.25 | 0.13 | 0.38 |
| Ipa1/Ipa1/Ipa1 | 137 | 1.01 | 0.03 | 0.66 | 0.69 |
| SE | 7 | 0.06 | 0.07 | 0.09 | 0.09 |

[a]+/+ and Ipa1/Ipa1, diploid germ genotype; +/+/+ and Ipa1/Ipa1/Ipa1, triploid endosperm genotype.

TABLE 3

Summary of Ipa1 and Ipa2 $F_2$ and test-cross results

| Mutant[a] | Total kernels tested | Gametes tested[b] | Kernel Number[c] WT | Kernel Number[c] M | Chi-Sq.[d] | Mean dry Weight WT | Mean dry Weight M | Dry Weight Reduction[e] % |
|---|---|---|---|---|---|---|---|---|
| $F_2$ Results | | | | | | | | |
| Ipa1 | 1037 | — | 832 | 205 | 15.1** | 294 | 265 | 10.0 |
| Ipa2 | 400 | — | 316 | 84 | 3.4 | 272 | 253 | 9.3 |
| Reciprocol Test-Cross Results | | | | | | | | |
| Ipa1 | 1297 | F | 654 | 643 | 0.1 | 284 | 248 | 13.0 |
| | 1073 | M | 577 | 496 | 6.1** | 233 | 194 | 17.0 |
| Ipa2 | 676 | F | 324 | 352 | 1.2 | 295 | 280 | 5.0 |
| | 451 | M | 228 | 223 | 0.1 | 202 | 233 | 11.0 |

[a]Individual $F_1$ plants heterozygous for the indicated mutant were either self-pollinated to produce $F_2$ progenies or used both as male and female parent in reciprocol test-crosses (male and female gametes tested, respectively).
[b]M = male, F = Female.
[c]WT = wild-type, M = mutant.
[d]In the case of $F_2$s, a 3:1 model was tested. In the case of test-crosses, a 1:1 model was tested.
[e]DW Reduction: Kernel dry weight reduction is calculated as the difference between wild-type mean dry weight and mutant mean dry weight, divided by wild-type mean dry weight.

I claim:

1. A non-lethal, mutant soybean seed characterized by low phytic acid expression relative to wild-type soybean seed.

2. The seed of claim 1 wherein said seed is fully mature.

3. The seed of claim 1 wherein the genome of said seed is homozygous for the mutation responsible for said low phytic acid expression.

4. Germplasm which will yield the seed of claim 1.

5. A plant produced by the seed of claim 1.

* * * * *